(12) United States Patent
Allen et al.

(10) Patent No.: US 6,236,457 B1
(45) Date of Patent: May 22, 2001

(54) SPECTROSCOPIC ANALYSIS

(75) Inventors: Brian Lawrence Allen, Berwick; Michael Ron Hammer, Sassafras, both of (AU)

(73) Assignee: Varian Australia Pty. Ltd., Mulgrave (AU)

(*) Notice: Subject to any disclaimer, the term of this patent is extended or adjusted under 35 U.S.C. 154(b) by 0 days.

(21) Appl. No.: 09/180,380
(22) PCT Filed: Mar. 6, 1998
(86) PCT No.: PCT/AU98/00143
 § 371 Date: Aug. 9, 1999
 § 102(e) Date: Aug. 9, 1999
(87) PCT Pub. No.: WO98/40708
 PCT Pub. Date: Sep. 17, 1998

(30) Foreign Application Priority Data

Mar. 7, 1997 (AU) .................................................. PO 5511

(51) Int. Cl.[7] ................................ G01J 3/42; G01J 3/28
(52) U.S. Cl. .............................................. 356/328; 356/326
(58) Field of Search ..................................... 356/328, 310, 356/326, 329, 330–334, 305, 307, 302, 432

(56) References Cited

U.S. PATENT DOCUMENTS

| 5,477,322 | 12/1995 | Webster | 356/328 |
| 5,594,547 | 1/1997 | Rödel et al. | 356/312 |

FOREIGN PATENT DOCUMENTS

| 40792/78 | 4/1980 | (AU) . |
| 29060/84 | 12/1984 | (AU) . |
| 423 736 A2 | 4/1991 | (EP) . |
| 506 603 A2 | 9/1992 | (EP) . |

Primary Examiner—Robert H. Kim
Assistant Examiner—Michael P. Stafira
(74) Attorney, Agent, or Firm—Bella Fishman; Edward H. Berkowitz

(57) ABSTRACT

Spectroscopic apparatus for sequentially detecting the presence of a plurality of elements in a sample. The apparatus includes a plurality of lamps (1a–1e) each of which is for detecting the presence of a respective at least one predetermined element in a plurality of elements. A beam selector (13) which may be a mirror, is operative to direct a beam of light (7) from any one of lamps (1a–1e) to an analysis zone (8). The apparatus includes a monochromator (15), the drive (24) of which is under the control of a controller (25) with a memory device (26) linked thereto. Predetermined settings for the monochromator corresponding to the peak settings for each wavelength of interest can be stored in memory (26) for subsequently driving the monochromator to those settings without the need to undertake a peaking routine for each elemental analysis, thereby saving analyses time. The lamp and beam selector arrangement of the apparatus substantially reduces the time required to change from one lamp to another thereby facilitating sequential spectroscopic multi-element analyses of samples. Apparatus which uses a flame for atomising a sample includes valves (19 and 20) for controlling the flow of oxidant (17) and fuel (18) gases to a spray chamber (23) and then analysis zone (8), the oxidant (17) being supplied via a nebuliser (22). The valves (19 and 20) are preferably high speed oscillating valves having an adjustable on to off time ration under the control of a microprocessor (21). The oscillating valves (19 and 20) allow rapid changes to be made to the oxidant and fuel gas flows, thereby also saving analysis time.

15 Claims, 3 Drawing Sheets

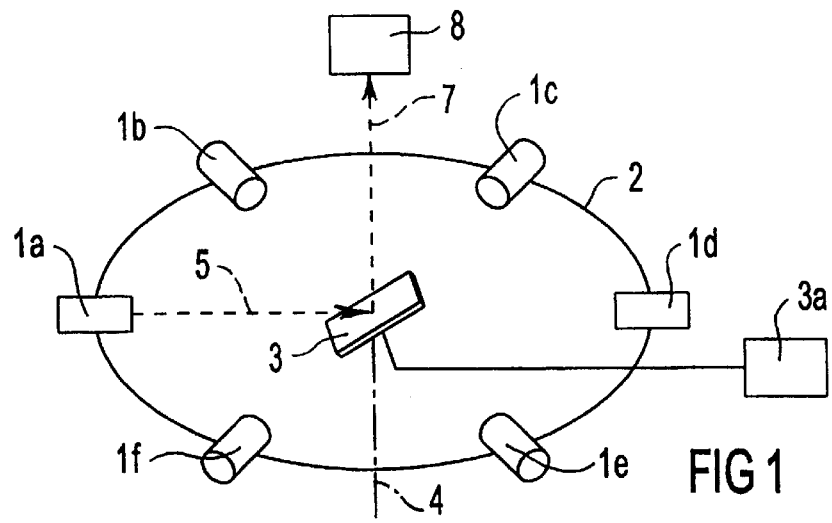
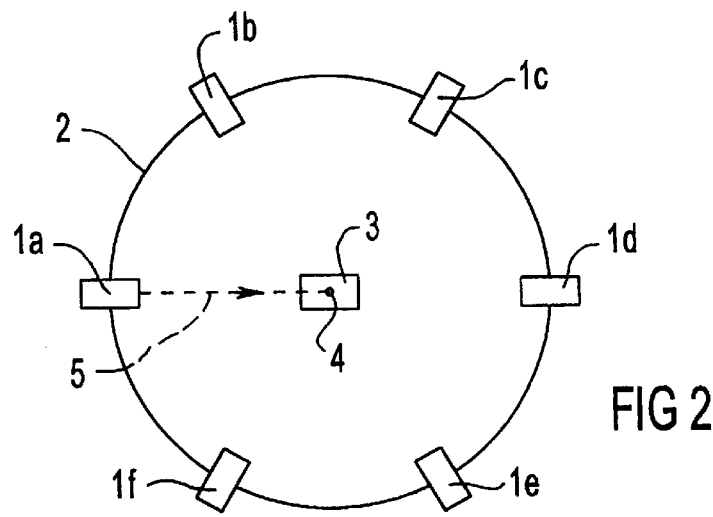
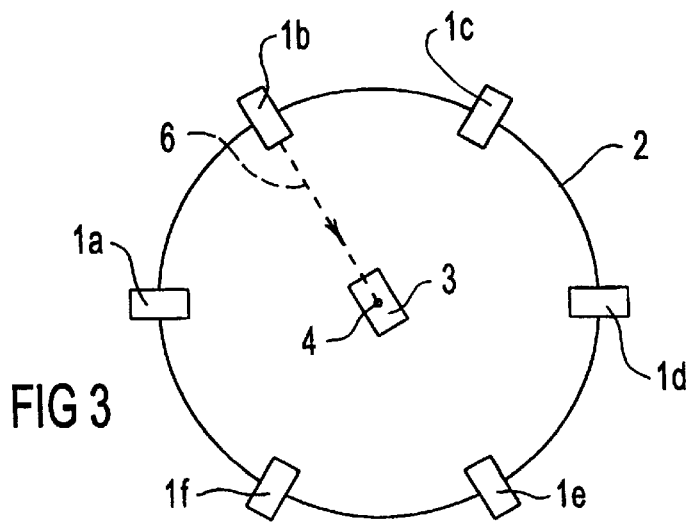

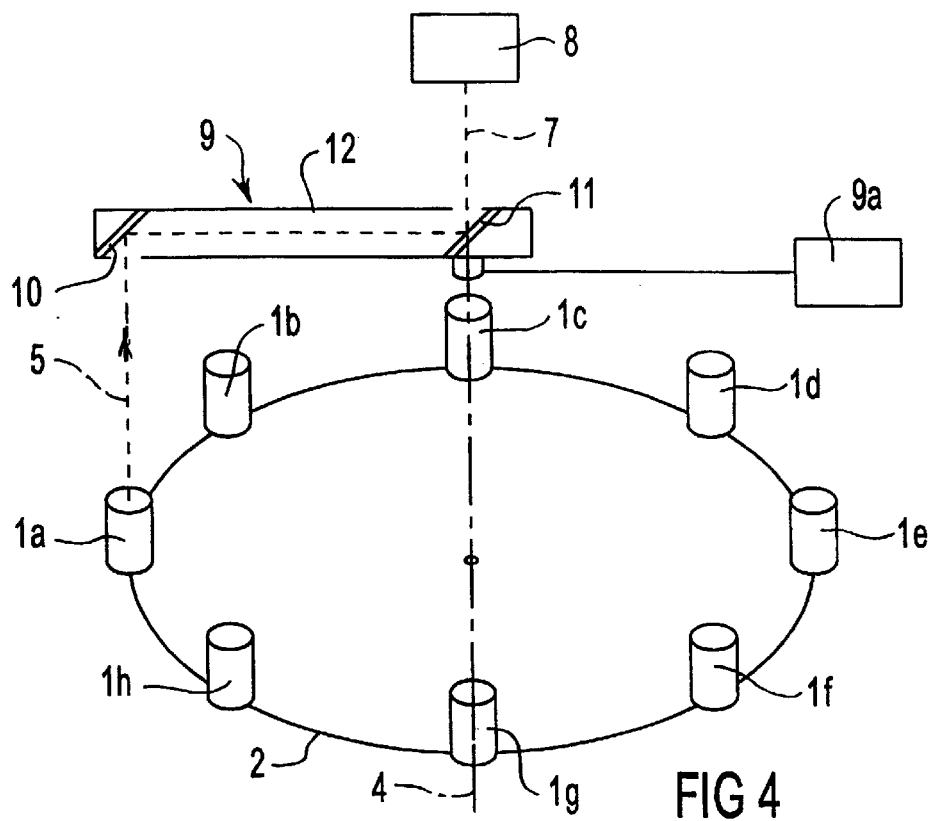
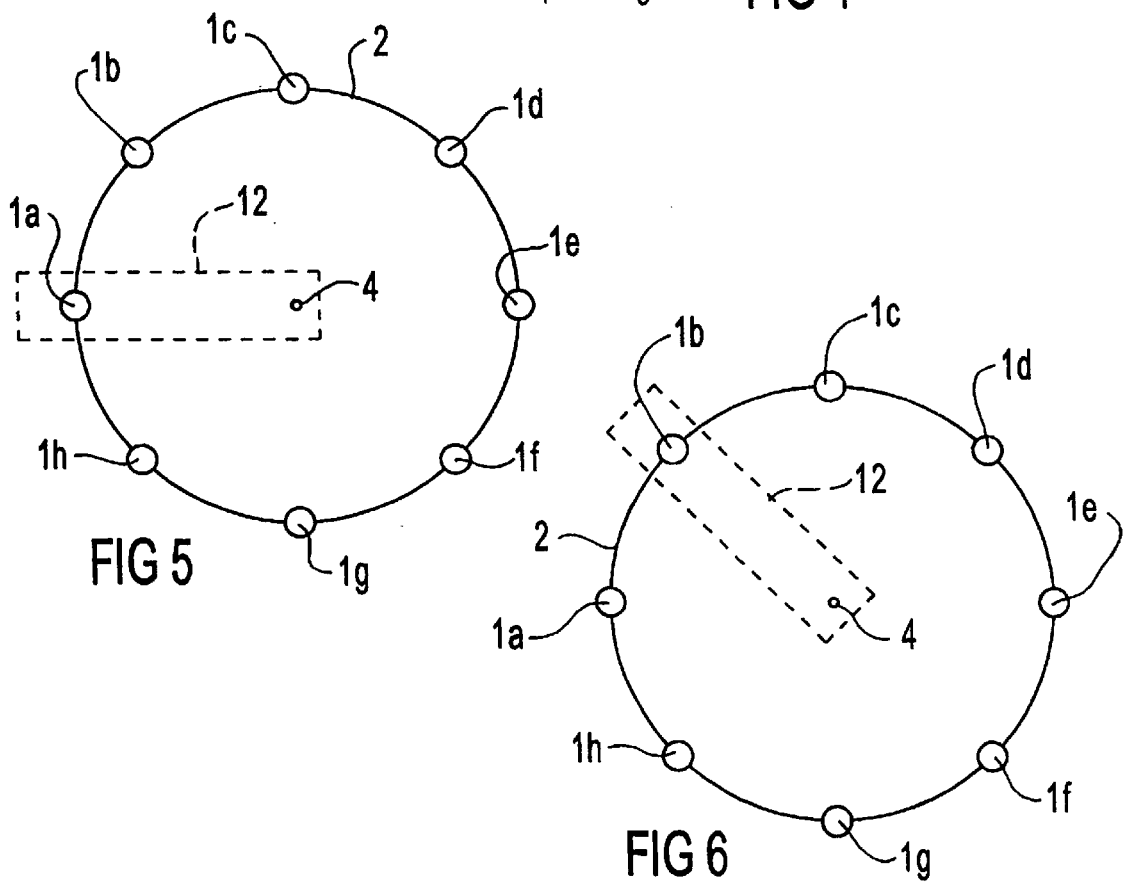

SPECTROSCOPIC ANALYSIS

TECHNICAL FIELD

This invention relates to spectroscopic analysis of a sample for the purpose of determining the presence of elements of interest in that sample. The invention is particularly concerned with analysis of a sample to determine the presence of two or more elements of interest.

It will be convenient to hereinafter describe the invention with particular reference to atomic absorption (AA) spectroscopy, but it is to be understood that the invention has wider application.

BACKGROUND

In elemental analysis, it is common for an analyst to be interested in determining concentrations of several elements for each sample. Since the focus for the analyst is the sample, the optimum arrangement would be for the system to determine all results pertaining to each sample as the sample is presented. Notwithstanding this, most current multi-element AA instrumentation operates by analysing all samples in sequence for the first element, followed by analysis of all samples in sequence for the second element, and so on. This method of operation while well entrenched is of considerable inconvenience to an analyst.

For this reason, a simultaneous multi-element AA system, capable of simultaneously analysing for all elements of interest as a sample is presented, has long been a goal of instrument manufacturers. Unfortunately such a system has proven extremely difficult to achieve at reasonable cost.

Prior to the present invention it has not been practical to change quickly some of the instrument operating conditions from those appropriate to one element of interest to those appropriate to another element of interest. In particular, a significant period of time is required to:

change from one lamp to another, change the fuel and oxidant gas flows (in flame atomisation spectrophotometers), and change from one wavelength to another.

The long delays involved in making changes of the foregoing kind have been considered unacceptable because of the consequent reduction in overall throughput and the excessive use of each sample.

SUMMARY OF THE INVENTION

According to the invention there is provided spectroscopic apparatus for sequentially detecting the presence of a plurality of elements in a sample including, a plurality of lamps, each of which is for generating a beam of light for detecting the presence of a respective at least one predetermined element of a plurality of elements, a beam selector and operating means for the beam selector, and an analysis zone at which a sample to be analysed is presentable, wherein each of the plurality of lamps occupies a fixed position relative to the analysis zone, and wherein the beam selector is operable. by the operating means to direct a beam of light from any one of the plurality of lamps to the analysis zone, and further including a monochromator for separating the analysis beam of light into different wave lengths, and controllable drive means for the monochromator for driving the monochromator to a predetermined setting which corresponds to a peak setting for each wavelength of interest.

A method according to the invention involves the use of a plurality of lamps, each of which is appropriate for detecting the presence of a respective at least one of a plurality of elements of interest and has a fixed position relative to a zone at which a sample to be analysed is presented for analysis. The method includes the steps of energising each lamp, either sequentially or simultaneously, so as to generate a beam of light from each lamp, and operating a beam selector so that it receives a selected one of the beams and directs that beam to the analysis zone. The arrangement is such that each beam of light can be directed to the analysis zone in turn so that a sample at that zone can be sequentially analysed for the presence of two or more elements of interest before another sample is presented to the analysis zone. The method additionally includes predetermining peak settings of the monochromator for each wavelength of interest and storing those peak settings for quickly driving the monochromator to a peak setting for a measurement.

An apparatus and method as described above substantially reduces the period of time required to change from one lamp to another and, for embodiments of the invention which provide for the sequential analysis of a number of samples, provides a relatively convenient and inexpensive solution for undertaking sequential spectroscopic multi-element analysis of those samples. In conventional AA spectroscopy the monochromator is driven to a wavelength of interest and is then peaked at that wavelength. Peaking involves scanning the monochromator over a small wavelength range and noting the setting which yields the highest light throughput. The monochromator is then driven to that setting for the measurement. This is a time consuming operation and cannot be started until the lamp of interest is stably positioned in the optical beam. The time taken to peak as well as being long is also additive to the time taken to change the lamp and typically is repeated for each measurement. Repetitive peaking time of the foregoing kind is avoided by executing a peaking routine for each element at the start of the batch analysis and storing in a memory the exact drive motor position corresponding to each peak. For subsequent monochromator movements the motor can be driven to a predetermined position without further peaking being required. By way of example, the monochromator drive motor may be a stepping motor and the motor position corresponding to a peak setting of the monochromator may be stored in software as the motor step count. In the case of very long batch runs there is a possibility of monochromator drift and this may require periodic readjustment of the peak settings. Such occasional re-adjustment does not add substantially to the overall batch time, whereas re-peaking on every movement does add very substantially to the batch run time.

In a preferred arrangement the beam selector includes a mirror which is movable relative to each of the lamps and which can adopt any one of a number of positions, each of which enables the mirror to receive a beam of light from a respective one of the lamps and direct that beam to the analysis zone of the apparatus.

Adoption of the foregoing technique enables lamp selection time to be reduced to less than 1 second, whereas conventional systems typically require a change over time of more than 10 seconds.

According to one arrangement the lamps are arranged radially in a circle or an arc of a circle, and the beam selector is located at the center of the circle and is movable about the circle axis so as to adopt any one of a plurality of operative positions. At each of the operative positions the beam selector is operative to receive a beam of light from a respective one of the lamps and direct that beam to the analysis zone. Other arrangements are clearly possible. By way of example, the lamps could be arranged in an arc or a straight line so that each has a fixed position relative to the others and relative to the analysis zone, and the beam selector is movable relative to the array of lamps so as to adopt any one of a plurality of operative positions as previously mentioned. It will, of course, be realised that for lamp arrangements wherein the lamps do not have an equal length optical path to the analysis zone additional focussing means to the focussing means that is normally present will be required for ensuring a lamp source is correctly imaged at the analysis zone.

In a form of the apparatus which uses a flame for atomising a sample, the apparatus can include means for feeding a fuel gas and means for feeding an oxidant gas to the analysis zone, wherein the fuel and oxidant gas flows are controlled by high speed regulating valves, preferably oscillating metering valves. In this form of the apparatus, the on to off time ratio of each valve can be adjusted as required to suit a respective one of two or more elements of interest. Such an arrangement enables appropriate adjustment of a valve to be achieved in a single oscillation cycle. By way of example, adoption of an oscillation frequency of approximately 33 Hertz allows gas flow to be changed in approximately 30 milliseconds. It will be appreciated that higher or lower frequencies could be used in practice. A period of stabilisation may need to be allowed before commencing analysis after each valve adjustment, and the length of that period will depend largely on the gas capacity of the system, but a period of less than 1 second would be typical. Thus this form of the apparatus reduces the period of time required to change the fuel and oxidant gas flows.

It will be convenient to hereinafter describe the invention in further detail by reference to the accompanying drawings which are diagrammatic representations of example embodiments of the invention. The particularity of the attached drawings and the related description is not to be understood as superseding the generality of the preceding broad description of the invention.

BRIEF DESCRIPTION OF DRAWINGS

FIG. 1 is a diagrammatic representation of one embodiment of a lamp and beam selector arrangement for use in spectroscopic apparatus according to the invention.

FIGS. 2 and 3 are diagrammatic plan views of the arrangement of FIG. 1 for illustrating the operation of the beam selector.

FIG. 4 is a diagrammatic representation of another embodiment of a lamp and beam selector arrangement for use in spectroscopic apparatus according to the invention.

FIGS. 5 and 6 are diagrammatic plan views of the arrangement of FIG. 4 for illustrating the operation of the beam selector.

DETAILED DESCRIPTION OF EMBODIMENTS

Figure 7:
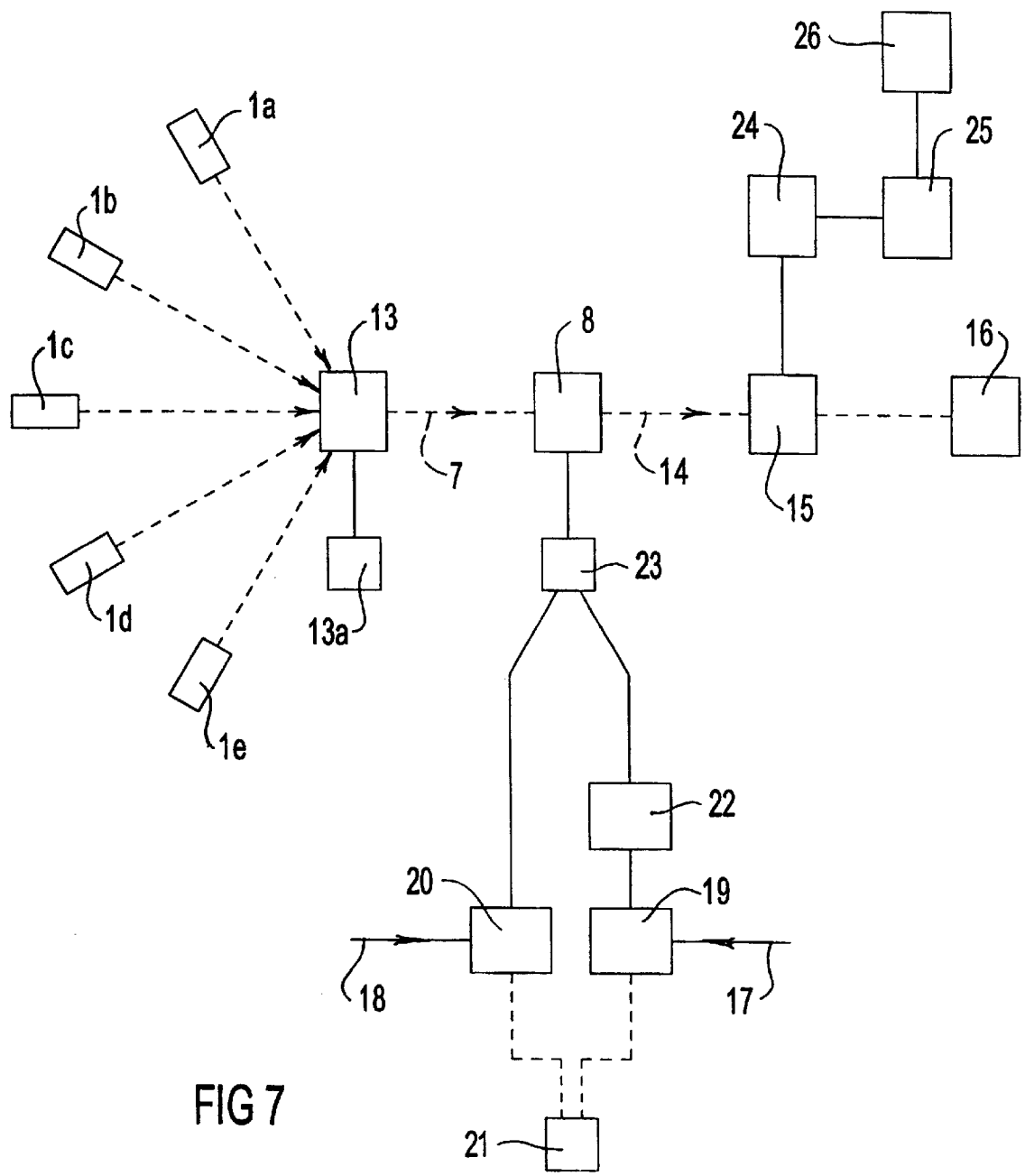
FIG. 7 is a diagrammatic representation of an AA spectrometry system illustrating further features of the invention.

FIG. 1 is a diagrammatic representation of one lamp and beam selector arrangement in which a number of lamps 1a to 1f, which may be hollow cathode lamps or other suitable spectral lamp sources, are arranged in an arc of a circle 2 and a beam selector in the form of a mirror 3 is positioned at the center of that circle. The beam selector is operable by an operating means 3a, which may be a motor for rotating the mirror 3. The number of lamps can be less or greater than that shown, and the lamps need not extend around the full circumference of the circle 2.

The mirror 3 is mounted for rotation about an axis 4 which is coincident with the center of the circle 2 so as to be positionable to receive a beam of light from any one of the lamps 1. FIG. 2 is a diagrammatic plan view which shows the mirror 3 positioned to receive a beam of light 5 from the lamp 1a, and FIG. 3 shows the mirror 3 positioned to receive a beam of light 6 from the lamp 1b. Each lamp I may be energised in sequence to generate a beam of light (in which case the energisation is synchronised with operation of the beam selector to ensure that light from the energised lamp is directed to the analysis zone), or all lamps 1 may be energised at the same time. As is evident from FIG. 1 the mirror 3 is operative to produce a reflected beam 7 which is directed to an analysis zone 8 (as is known, the apparatus includes focussing optics (not shown) for focussing the light at the analysis zone), and in the case of AA spectroscopy that analysis zone may include a flame or a graphite furnace.

FIGS. 4 to 6 show another arrangement in which the lamps 1 are arranged to direct their respective beams axially of the circle 2 rather than radially as shown by FIGS. 1 to 3. In this arrangement the beam selector includes a mirror assembly 9 or other appropriate means which is rotatable about the axis 4 by an operating means 9a. The particular assembly 9 as shown includes a first mirror 10 which receives the beam of light from a selected lamp 1, and a second mirror 11 which is positioned at the axis 4. Both mirrors 10 and 11 are mounted within a housing 12 and rotate with that housing about the axis 4.

As shown by FIGS. 5 and 6 the rotational position of the housing 12 determines which lamp 1 will be operative for analysis purposes at any particular time. In the position shown by FIGS. 4 and 5 the assembly 9 is arranged to receive a beam 5 from the lamp 1a, and the mirror 10 reflects that beam to the mirror 11 which is turn produces the reflected beam 7 which is directed to the analysis zone 8. FIG. 6 shows the assembly 9 rotated to a different position at which it receives a beam of light from the lamp 1b and reflects that beam to the analysis zone 8.

FIG. 7 is a diagrammatic representation of an AA system incorporating a bank of lamps 1a to 1e and a beam selector 13 which may be of any suitable form including one having a mirror or mirrors as previously described. The beam select6r 13 is operable by an operating means 13a to transmit a beam of light 7 derived from a selected one of the lamps 1, to the analysis zone 8, which may include a flame atomisation arrangement or a graphite furnace each of which operates in a known manner. The beam 7 is typically focussed at zone 8 by focussing means (not shown). A residuum beam 14 is then passed through a monochromator 15 to a detector 16, each of which operates in a known manner.

For a flame atomisation arrangement, an oxidant gas and a fuel gas may be delivered to the analysis zone 8 along respective flow paths 17 and 18 as shown. It is preferred that the flow of each gas is regulated by a respective one of two high speed valves 19 and 20, and it is further preferred that each valve 19 and 20 is an oscillating metering valve having an adjustable on to off time ratio. One such valve is the subject of U.S. Pat. No. 5,355,214, and the disclosure of the specification of that patent, or the Australian equivalent Patent 651367, is to be understood as incorporated into the present specification by cross reference. Each of the valves 19 and 20 may be controlled through a micro-processor 21 or other suitable control means to enable variation of the on to off time ratio as necessary to suit prevailing operating circumstances or conditions of the system represented by FIG. 7. In the particular arrangement shown by FIG. 7 the valve 19 is operative to deliver oxidant to the analysis zone 8 by way of a nebuliser 22 and spray chamber 23, each of which operates in a known manner. The valve 20 also delivers the fuel gas to the analysis zone 8 by way of the spray chamber 23. It is preferred that the nebuliser 22 is constructed in accordance with the disclosure of Australian provisional patent application No. PO 5513 filed on Mar. 7, 1997 and which is entitled "Spectroscopic Atomisation Assembly".

The system of FIG. 7 includes a drive means 24 for the monochromator 15 which is controlled by a controller 25 in such a manner that the monochromator 15 can be quickly driven to the peak setting for each particular wavelength of interest. As a particular peak setting is determined for each wavelength of interest the parameters which establish each such setting may be stored in memory through appropriate means such as a micro-processor 26. The stored information can then be used as required to quickly set the monochromator 15 for each wavelength as selected for a particular analysis cycle. The drive means 24 may include a stepper motor.

It will be evident from the foregoing description that the present invention provides a convenient and relatively inexpensive system for undertaking sequential spectroscopic mulelement analysis of a number of samples.

The invention also provides spectroscopic apparatus which can be conveniently transferred between two or more setup conditions, each of which is appropriate for a respective one of two or more elements of interest which may be present in a sample to be analysed. The invention also provides a method and apparatus for conducting spectroscopic analysis of two or more samples in sequence and which enables each sample to be analysed for the presence of two or more elements of interest before another sample is presented for analysis.

In use of an instrument according to the invention for a typical analysis, the analyst must select the elements to be determined and the most appropriate emission line wavelength(s) and bandwidth for each element. Sufficient spectral source lamps (typically hollow cathode lamps, although other spectral sources may be used) for the elements to be measured are then fitted to the instrument. According to one embodiment the source lamps include electrical coding means to identify the particular element(s) spectra which the lamp will emit and the instrument electronics detects which lamp location the source for a particular element is located in. In other embodiments this information must be manually entered by the analyst.

To optimise the speed of analysis, it is necessary to determine the fastest means of setting the monochromator to the required wavelength and bandwidth (eg. slit setting), whilst selecting the appropriate source lamp. As the monochromator is generally slower to move than the beam selector, the fastest analysis is achieved by carrying out the analysis in wavelength order and directing the beam selector to the appropriate lamp source as each new wavelength is reached. However, a different analysis order may be required to achieve a mrinimum analysis time depending on the response speed of the monochromator, beam selector and other components.

Variations, modifications and/or additions other than those specifically described may be made to the invention described herein and it is to be understood that the invention includes all such variations, modifications and/or additions which fall within the scope of the following claims.

What is claimed is:

1. Spectroscopic apparatus for sequentially detecting the presence of a plurality of elements in a sample said apparatus comprising, a plurality of lamps, each of which is for generating a beam of light for detecting the presence of a respective at least one predetermined element of a plurality of elements, a beam selector and operating means for the beam selector, and an analysis zone at which a sample to be analyzed is presentable, wherein each of the plurality of lamps occupies a fixed position relative to the analysis zone said lamps being radially arranged relative to an axis such that they lie in a circle or circular arc having a centre on the axis. and wherein the beam selector is operable by the operating means to direct a beam of light from any one of the plurality of lamps to the analysis zone. said beam selector being movable about said axis and positionable into any one of a plurality of positions, wherein at each position the beam selector receives a beam of light from a respective one of the lamps and direct that beam to the analysis zone. wherein the lamps are arranged to direct their beams axially parallel to said axis. and the beam selector directs the axial beam it receives from each lamp along said axis, and further comprising a monochromator for separating the analysis beam of light into different wave lengths, and controllable drive means for driving the monochromator to a perdetermined setting which corresponds to a peak setting for each wavelength of interest.

2. A method for operating spectroscopic apparatus capable of sequentially analyzing a sample to determine the presence of a plurality of elements in said sample through response of said sample to a radiation beam obtained from a selected one of a plurality of lamps and a beam selector for selectively directing said radiation beam to said sample, comprising the steps of (a) transporting said sample to an analysis zone,
(b) sequentially energizing each said lamp, operating said beam selector synchronously with said step of energizing whereby to illuminate said sample in turn with a radiation beam from each lamp,
(c) sequentially analyzing a first sample at the analysis zone for the presence of a pluralitv of elements and then presenting a second sample at the analysis zone and sequentially analysing the second sample for the presence of a plurality of elements,
i) in relation to said first sample in the analysis zone. finding a peak setting for the monochromator for each wavelength for the elements of interest, wherein each peak setting provides the highest light throughput for the selected wavelength for the respective elements of interest,
ii) storing information which represents each peak setting,
iii) presenting said second sample at the analysis zone and during its analysis, driving the monochromator to each predetermined peak setting as determined by the stored information thereby avoiding step (i) for the second sample, and
iv) repeating step (iii) in respect of subsequent samples.

3. A method for operating spectroscopic apparatus capable of sequentially analyzing a sample to determine the presence of a plurality of elements in said sample through response of said sample to a radiation beam obtained from a selected one of a plurality of lamps and a beam selector for selectively directing said radiation beam to said sample, comprising the steps of (a) transporting said sample to an analysis zone, (b) simultaneously energizing each said lamp, (c) operating said beam selector so that it receives, in turn, a radiation beam from each said lamp and directs that beam to said analysis zone for sequentially analyzing for the presence of two or more elements in said sample, (d) sequentially analyzing a first sample at the analysis zone for the presence of a plurality of elements and then presenting a second sample at the analysis zone and sequentially analyzing the second sample for the presence of a plurality of elements, (e) i) in relation to said first sample in the analysis zone, findinlg a peak setting for the monochromator for each wavelength for the elements of interest. wherein each peak setting provides the highest light throughput for the selected wavelength for the respective elements of interest, ii) storing information which represents each peak setting, iii) presenting said second sample at the analysis zone and during its analysis, driving the monochromator to each predetermined peak setting as determined by the stored information thereby avoiding step (i) for the second sample, and iv) repeating step (iii) in respect of subsequent samples.

4. Spectroscopic apparatus for sequentially detecting the presence of a plurality of elements in a sample said apparatus comprising, a plurality of lamps, each of which is for generating a beam of light for detecting the presence of a respective at least one predetermined element of a plurality of elements, a beam selector and operating means for the beam selector, and an analysis zone at which a sample to be analyzed is presentable, wherein each of the plurality of lamps occupies a fixed position relative to the analysis zone said lamps being radially arranged relative to an axis such that they lie in a circle or circular arc having a centre on the axis, and wherein the beam selector is operable by the operating means to direct a beam of light from any one of the plurality of lamps to the analysis zone, said beam selector being movable about said axis and positionable into any one of a plurality of positions, wherein at each position the beam selector receives a beam of light from a respective one of the lamps and direct that beam to the analysis zone, wherein the lamps are arranged to direct their beams radially with respect to said axis, and the beam selector redirects the radial beam it receives from each lamp along said axis, and further comprising a monochromator for separating the analysis beam of light into different wave lengths, and controllable drive means for driving the monochromator to a predetermined setting which corresponds to a peak setting for each wavelength of interest.

5. Spectroscopic apparatus of claim 1 or 4 wherein the beam selector is a mirror.

6. Spectroscopic apparatus claim 5 wherein the beam selector includes at least two mirrors.

7. Spectroscopic apparatus of claim 1 or 4 wherein the controllable drive means includes a memory storage device for storing information for determining settings for the monochromator which settings correspond to a peak position for each wavelength.

8. Spectroscopic apparatus of claim 7 wherein the controllable drive means includes a drive motor which is controllable by the memory storage device.

9. Spectroscopic apparatus of claim 8 wherein the drive motor is a stepper motor.

10. Spectroscopic apparatus of claim 1 or 4 further comprising a flame atomisation arrangement for atomising the sample at the analysis zone and means for feeding a fuel gas and means for feeding an oxidant gas to said arrangement, wherein a high speed regulating valve is included in each said feeding means.

11. Spectroscopic apparatus of claim 10 wherein the regulating valves are oscillating metering valves having an adjustable on to off time ratio.

12. Spectroscopic apparatus of claim 11 including control means for the regulating valves for varying the on to off time ratio of the valves.

13. Spectroscopic apparatus of claim 12 including means for sequentially presenting samples to the analysis zone.

14. The method of claim 2 or 3 further comprising flame atomising said sample, said flame atomizing comprising adjusting the flow rate of a fuel gas to said analysis zone, adjusting the flow rate of an oxidant gas to said analysis zone and adjusting each said flow rate in respect to each said element.

15. The method of claim 14 wherein said adjustment of flow rate is accomplished within approximately 30 milliseconds.

* * * * *